(12) United States Patent
De Bodinat

(10) Patent No.: US 7,902,180 B2
(45) Date of Patent: *Mar. 8, 2011

(54) ASSOCIATION BETWEEN AGOMELATINE AND A THYMOREGULATORY AGENT AND PHARMACEUTICAL COMPOSITIONS CONTAINING IT

(75) Inventor: Christian De Bodinat, Saint-Cloud (FR)

(73) Assignee: Les Laboratoires Servier, Suresnes Cedex (FR)

( * ) Notice: Subject to any disclaimer, the term of this patent is extended or adjusted under 35 U.S.C. 154(b) by 144 days.

This patent is subject to a terminal disclaimer.

(21) Appl. No.: 11/516,992

(22) Filed: Sep. 7, 2006

(65) Prior Publication Data
US 2007/0066689 A1    Mar. 22, 2007

(30) Foreign Application Priority Data

Sep. 9, 2005   (FR) ...................................... 05 09208

(51) Int. Cl.
| | |
|---|---|
| A61K 31/33 | (2006.01) |
| A61K 31/194 | (2006.01) |
| A61K 31/235 | (2006.01) |
| A61K 31/426 | (2006.01) |
| A61P 3/10 | (2006.01) |

(52) U.S. Cl. ........................................................ 514/183
(58) Field of Classification Search .................. 514/558
See application file for complete search history.

(56) References Cited

U.S. PATENT DOCUMENTS 6,395,780 B1 *   5/2002   Arlt et al. ...................... 514/557

OTHER PUBLICATIONS

JD. Guelfi, et al., "Efficacy and safety of the new antidepressant agomelatine in combination with a mood stabilizer in bipolar I patients with a major depressive episode" Bipolar Disorders, vol. 7, No. Suppl. 2, p. 62, Jun. 2005.
Chilman-Blair, et al., "Agomelatine. Antidepressant treatment of bipolar disorder melatonin agonist/5-HT20 antagonist", Drugs of the Future, vol. 28, No. 1, p. 7-13, Jan. 2003.
French Preliminary Search Report for 05.09208 of Apr. 27, 2006.

* cited by examiner

*Primary Examiner* — Ardin Marschel
*Assistant Examiner* — Alicia R Hughes
(74) *Attorney, Agent, or Firm* — Hueschen and Sage

(57) ABSTRACT

Association comprising agomelatine, or N-[2-(7-methoxy-1-naphthyl)ethyl]acetamide, in association with a thymoregulatory agent.
Medicinal products containing the same which are useful in the treatment of mood disorders.

2 Claims, No Drawings

ASSOCIATION BETWEEN AGOMELATINE AND A THYMOREGULATORY AGENT AND PHARMACEUTICAL COMPOSITIONS CONTAINING IT

The present invention relates to a new association between agomelatine, or N-[2-(7-methoxy-1-naphthyl)ethyl]acetamide of formula (I):

or its hydrates, crystalline forms and addition salts with a pharmaceutically acceptable acid or base, and a thymoregulatory agent for obtaining pharmaceutical compositions for use in the treatment of mood disorders and, more especially, major depressive disorder, cyclothymic disorder and dysthymic disorder.

Agomelatine, or N-[2-(7-methoxy-1-naphthyl)ethyl]acetamide, has the double characteristic of being, on the one hand, an agonist of receptors of the melatoninergic system and, on the other hand, an antagonist of the 5-HT$_{2c}$ receptor. These properties provide it with activity in the central nervous system and, more especially, in the treatment of major depressive disorder, seasonal affective disorder, sleep disorders, cardiovascular pathologies, pathologies of the digestive system, insomnia and fatigue due to jet-lag, appetite disorders and obesity.

Agomelatine, its preparation and its use in therapeutics have been described in European Patent Specification EP 0 447 285.

The Applicant has now found that agomelatine, or N-[2-(7-methoxy-1-naphthyl)ethyl]-acetamide or its hydrates, crystalline forms and addition salts with a pharmaceutically acceptable acid or base, used in association with a thymoregulatory agent, has valuable properties allowing its use in the treatment of mood disorders and, more especially, major depressive disorder, cyclothymic disorder and dysthymic disorder.

Disorders of the central nervous system, such as mood disorders, affect a large number of people of all ages. They are so named because of the implication of persistent positive or negative affects of sufficiently severe intensity to produce maladapted behaviour.

Major depressive disorder is an acute and severe mood disorder characterised by sadness, pessimism, notions of suicide, an ideomotor slow-down and various somatic complaints. Extremely handicapping, it may lead to cessation of all functional or social activity. Added to the suffering of the depressed subject himself is the suffering of the family circle. Cyclothymic disorder is characterised by the repetitive occurrence of positive (expansive mood) and negative (depressive mood) thymic variations which are less severe than those of bipolar disorder, with less functional impairment; the difficulty of diagnosis, however, is real, and some elements lead to the belief that cyclothymic disorder is the precursor of bipolar disorder. The association of an antidepressant and a thymoregulator allows thymic variations to be controlled and prevents them from developing into a characterised bipolar disorder.

Finally, dysthymic disorder is a chronic and intense mood disorder that is characterised by long periods of dysphoric mood and functional impairment. Just as for professional exhaustion syndrome, the other symptoms of dysthymia may include the following feelings: lack of adaptation, despair, irritability or excessive anger, guilt, loss of interest or of general pleasure, social withdrawal, chronic fatigue, decline in activity or productivity and poor concentration. Dysthymia is an insidious mental disorder. In contrast to the disabling functional symptoms associated with diseases such as major depressive disorder, subjects affected by dysthymia generally suffer from moderate social and professional dysfunction. For example, in spite of typical disturbances in their general interpersonal function, dysthymic subjects are often seen to work assiduously in their profession and maintain a facade of normality.

Although a large number of effective molecules exist in this field—thymoanaleptics and thymic regulators may be mentioned more especially—none allows those various pathological states to be treated with complete satisfaction, and a number of them have significant side effects. Accordingly, the development of new alternative treatments is ongoing and continues to be a necessity.

The Applicant has now discovered, surprisingly, that agomelatine used in association with a thymoregulatory agent has properties wholly suited to the treatment of mood disorders and, more especially, major depressive disorder, cyclothymic disorder and dysthymic disorder. Thymoregulators, generally described for their antimanic properties allowing them to act on the thymic expansiveness of manic states, are currently used in the treatment of bipolar disorders.

The Applicant has now discovered that those thymoregulatory agents exhibit the characteristic of potentiating the effects of agomelatine both in the field of depressive mood disorders and in that of manic disorders.

That unpredictable effect allows the use of the association according to the invention to be considered in the treatment of mood disorders and, more especially, major depressive disorder, cyclothymic disorder and dysthymic disorder.

Among the thymoregulatory agents according to the invention there may be mentioned more especially, without implying any limitation, lithium, carbamazepine, valproate and lamotrigine, and more preferably valproate.

The invention accordingly relates to the use of the association between agomelatine or its hydrates, crystalline forms and addition salts with a pharmaceutically acceptable acid or base, and a thymoregulatory compound in obtaining pharmaceutical compositions intended for the treatment of mood disorders and, more especially, major depressive disorder, cyclothymic disorder and dysthymic disorder.

The invention relates also to pharmaceutical compositions containing the association between agomelatine or its hydrates, crystalline forms and addition salts with a pharmaceutically acceptable acid or base, and a thymoregulatory compound in combination with one or more pharmaceutically acceptable excipients.

Among the pharmaceutical compositions according to the invention there may be mentioned, more especially, those which are suitable for oral, parenteral or nasal administration, tablets or dragées, sublingual tablets, gelatin capsules, lozenges, suppositories, creams, ointments, dermal gels etc.

Besides agomelatine and the thymoregulatory compound, the pharmaceutical compositions according to the invention comprise one or more excipients or carriers selected from diluents, lubricants, binders, disintegration agents, absorbents, colourants, sweeteners etc.

By way of example, and without implying any limitation, there may be mentioned:

as diluents: lactose, dextrose, sucrose, mannitol, sorbitol, cellulose, glycerol,
as lubricants: silica, talc, stearic acid and its magnesium and calcium salts, polyethylene glycol,
as binders: aluminium and magnesium silicate, starch, gelatin, tragacanth, methyl-cellulose, sodium carboxymethyl-cellulose and polyvinylpyrrolidone,
as disintegrants: agar, alginic acid and its sodium salt, effervescent mixtures.

The useful dosage varies according to the sex, age and weight of the patient, the administration route, the nature of the disorder and any associated treatments and ranges from 1 mg to 50 mg of agomelatine per 24 hours and is more preferably 25 mg per day. The dose of thymoregulatory agent will be less than that used when it is administered on its own.

Pharmaceutical Composition:

Formula for the preparation of 1000 tablets each containing 25 mg of active ingredient:

| | |
|---|---|
| N-[2-(7-methoxy-1-naphthyl)ethyl]acetamide | 25 g |
| Lactose monohydrate | 62 g |
| Magnesium stearate | 1.3 g |
| Povidone | 9 g |
| Anhydrous colloidal silica | 0.3 g |
| Cellulose sodium glycolate | 30 g |
| Stearic acid | 2.6 g |

Clinical Study:

The clinical study carried out uses international nomenclature, essentially DSM-IV, and also validated measurement tools, such as the Hamilton Scale of Depression, Young's mania scale, the Global Clinical Impression scale, which are all instruments recommended by the guidelines in force. Comparison of the agomelatine-valproate association versus thymoregulator placebo under best methodology conditions allows us to conclude that the association is superior.

The invention claimed is:

1. A composition comprising a combination of agomelatine, or N-[2-(7-methoxy-1-naphthyl)ethyl]acetamide or addition salts thereof with a pharmaceutically acceptable acid or base, and valproate.

2. A pharmaceutical composition comprising as active ingredient a composition of claim 1 alone or in combination with one or more pharmaceutically acceptable excipients.

* * * * *